(12) United States Patent
Kumar et al.

(10) Patent No.: US 9,255,913 B2
(45) Date of Patent: Feb. 9, 2016

(54) SYSTEM AND METHOD FOR ACOUSTICALLY IDENTIFYING DAMAGED SECTIONS OF A ROUTE

(71) Applicant: General Electric Company, Schenectady, NY (US)

(72) Inventors: Ajith Kuttannair Kumar, Erie, PA (US); Joseph Forrest Noffsinger, Grain Valley, MO (US); Edward James Nieters, Burnt Hills, NY (US)

(73) Assignee: General Electric Company, Schenectady, NY (US)

( * ) Notice: Subject to any disclaimer, the term of this patent is extended or adjusted under 35 U.S.C. 154(b) by 280 days.

(21) Appl. No.: 13/955,364

(22) Filed: Jul. 31, 2013

(65) Prior Publication Data

US 2015/0033864 A1    Feb. 5, 2015

(51) Int. Cl.
G01N 29/265    (2006.01)
G01N 29/14    (2006.01)
G01N 29/44    (2006.01)

(52) U.S. Cl.
CPC ............. *G01N 29/265* (2013.01); *G01N 29/14* (2013.01); *G01N 29/4454* (2013.01); *G01N 2291/2632* (2013.01)

(58) Field of Classification Search
CPC . G01N 29/265; G01N 29/4454; G01N 29/14; G01N 2291/2632
USPC ......................................................... 73/636
See application file for complete search history.

(56) References Cited

U.S. PATENT DOCUMENTS

| | | |
|---|---|---|
| 2,059,160 A | 10/1934 | Wintsch et al. |
| 2,628,335 A | 2/1953 | Drake et al. |
| 3,016,464 A | 1/1962 | Bailey et al. |
| 3,137,756 A | 6/1964 | Gunther et al. |
| 3,393,600 A | 7/1968 | Bess et al. |
| 3,517,307 A | 6/1970 | Wallen et al. |
| 3,562,419 A | 2/1971 | Stewart et al. |
| 3,589,815 A | 6/1971 | Hosterman |
| 3,594,912 A | 7/1971 | Sauterel |
| 3,604,359 A | 9/1971 | Doorley et al. |
| 3,633,010 A | 1/1972 | Svetichny |

(Continued)

FOREIGN PATENT DOCUMENTS

| | | |
|---|---|---|
| DE | 3538165 A1 | 4/1987 |
| DE | 4225800 C1 | 11/1993 |

(Continued)

OTHER PUBLICATIONS

Popov, Ing. Alexandr; "Automated Ultrasonic Inspection of Rails", STARMANS Electronics, s.r.o., Prague, CZ, www.starmans.net, 5 pgs.

(Continued)

*Primary Examiner* — J M Saint Surin
(74) *Attorney, Agent, or Firm* — GE Global Patent Operation; John A. Kramer

(57) ABSTRACT

A method for acoustically examining a route includes sensing passively excited residual sounds of a vehicle system during travel over a route, examining the passively excited residual sounds to identify one or more changes of interest in the passively excited residual sounds, and identifying a section of the route as being damaged responsive to the one or more changes of interest in the passively excited residual sounds that are identified.

20 Claims, 6 Drawing Sheets

(56) References Cited

U.S. PATENT DOCUMENTS

| | | |
|---|---|---|
| 3,696,243 A | 10/1972 | Risely |
| 3,821,558 A | 6/1974 | Mansfield |
| 3,821,932 A | 7/1974 | Theurer et al. |
| 3,828,440 A | 8/1974 | Plasser et al. |
| 3,850,390 A | 11/1974 | Geiger et al. |
| 3,864,039 A | 2/1975 | Wilmarth |
| 3,870,952 A | 3/1975 | Sibley |
| 3,875,865 A | 4/1975 | Plasser et al. |
| 3,896,665 A | 7/1975 | Goel |
| 3,924,461 A | 12/1975 | Stover |
| 3,937,068 A | 2/1976 | Joy |
| 3,960,005 A | 6/1976 | Vezina |
| 3,962,908 A | 6/1976 | Joy |
| 3,974,991 A | 8/1976 | Geiger |
| 3,987,989 A | 10/1976 | Geiger |
| 3,995,560 A | 12/1976 | Mackintosh |
| 4,005,601 A | 2/1977 | Botello |
| 4,022,408 A | 5/1977 | Staples |
| 4,040,738 A | 8/1977 | Wagner |
| 4,044,594 A | 8/1977 | Davidson et al. |
| 4,069,590 A | 1/1978 | Effinger |
| 4,117,529 A | 9/1978 | Ehrlich et al. |
| 4,143,553 A | 3/1979 | Hendricks et al. |
| 4,145,018 A | 3/1979 | Muratore et al. |
| 4,155,176 A | 5/1979 | Goel et al. |
| 4,165,648 A | 8/1979 | Pagano |
| 4,173,073 A | 11/1979 | Fukazawa et al. |
| 4,174,636 A | 11/1979 | Pagano |
| 4,181,430 A | 1/1980 | Ando et al. |
| 4,198,164 A | 4/1980 | Cantor |
| 4,207,569 A | 6/1980 | Meyer |
| 4,222,275 A | 9/1980 | Marshall et al. |
| 4,229,978 A | 10/1980 | Marshall et al. |
| 4,235,112 A | 11/1980 | Kaiser |
| 4,259,018 A | 3/1981 | Poirier |
| 4,288,855 A | 9/1981 | Panetti |
| 4,306,694 A | 12/1981 | Kuhn |
| 4,383,448 A | 5/1983 | Fujimoto et al. |
| 4,389,033 A | 6/1983 | Hardman |
| 4,391,134 A | 7/1983 | Hansmann et al. |
| 4,417,466 A | 11/1983 | Panetti |
| 4,417,522 A | 11/1983 | Bock et al. |
| 4,429,576 A | 2/1984 | Norris |
| 4,430,615 A | 2/1984 | Calvert |
| 4,457,178 A | 7/1984 | Meignan et al. |
| 4,467,430 A | 8/1984 | Even et al. |
| 4,468,966 A | 9/1984 | Bradshaw |
| 4,487,071 A | 12/1984 | Morris et al. |
| 4,490,038 A | 12/1984 | Riessberger et al. |
| 4,531,837 A | 7/1985 | Panetti |
| 4,538,061 A | 8/1985 | Jaquet |
| 4,541,182 A | 9/1985 | Panetti |
| 4,548,070 A | 10/1985 | Panetti |
| 4,577,494 A | 3/1986 | Jaeggi |
| 4,578,665 A | 3/1986 | Yang |
| 4,593,569 A | 6/1986 | Joy |
| 4,609,870 A | 9/1986 | Hocking et al. |
| 4,615,218 A | 10/1986 | Pagano |
| 4,625,412 A | 12/1986 | Bradshaw |
| 4,654,973 A | 4/1987 | Worthy |
| 4,655,142 A | 4/1987 | Bock et al. |
| 4,662,224 A | 5/1987 | Turbe |
| 4,689,995 A | 9/1987 | Turbe |
| 4,691,565 A | 9/1987 | Theurer |
| 4,700,223 A | 10/1987 | Shoutaro et al. |
| 4,700,574 A | 10/1987 | Turbe |
| 4,723,738 A | 2/1988 | Franke |
| 4,728,063 A | 3/1988 | Auer et al. |
| 4,735,384 A | 4/1988 | Elliott |
| 4,741,207 A | 5/1988 | Spangler |
| 4,763,526 A | 8/1988 | Pagano |
| 4,886,226 A | 12/1989 | Frielinghaus |
| 4,915,504 A | 4/1990 | Thurston |
| 4,932,618 A | 6/1990 | Davenport et al. |
| 4,979,392 A | 12/1990 | Guinon |
| 4,986,498 A | 1/1991 | Nayer et al. |
| 5,009,014 A | 4/1991 | Leach |
| 5,036,594 A | 8/1991 | Jordan et al. |
| 5,086,591 A | 2/1992 | Panetti |
| 5,094,004 A | 3/1992 | Wooten |
| 5,101,358 A | 3/1992 | Panetti |
| 5,134,808 A | 8/1992 | Panetti |
| 5,140,776 A | 8/1992 | Isdahl et al. |
| 5,161,891 A | 11/1992 | Austill |
| 5,199,176 A | 4/1993 | Eglseer et al. |
| 5,203,089 A | 4/1993 | Centil et al. |
| 5,253,830 A | 10/1993 | Durchschlag et al. |
| 5,275,051 A | 1/1994 | De Beer |
| 5,301,548 A | 4/1994 | Theurer |
| 5,339,692 A | 8/1994 | Ivachev et al. |
| 5,341,683 A | 8/1994 | Searle |
| 5,353,512 A | 10/1994 | Lichtberger et al. |
| 5,386,727 A | 2/1995 | Searle |
| 5,419,196 A | 5/1995 | Havira et al. |
| 5,429,329 A | 7/1995 | Swanson et al. |
| 5,433,111 A | 7/1995 | Hershey et al. |
| 5,452,222 A | 9/1995 | Ambrose et al. |
| 5,459,663 A | 10/1995 | Franke |
| 5,475,597 A | 12/1995 | Buck |
| 5,522,265 A | 6/1996 | Jaeggi |
| 5,529,267 A | 6/1996 | Boyle et al. |
| 5,574,224 A | 11/1996 | Havira et al. |
| 5,578,758 A | 11/1996 | Havira et al. |
| 5,579,013 A * | 11/1996 | Hershey ............... B61K 9/08 342/357.4 |
| 5,598,782 A | 2/1997 | Marriott et al. |
| 5,605,099 A | 2/1997 | Bradshaw et al. |
| 5,613,442 A | 3/1997 | Ahola et al. |
| 5,623,244 A | 4/1997 | Cooper |
| 5,627,508 A | 5/1997 | Anderson et al. |
| 5,628,479 A | 5/1997 | Ballinger |
| 5,636,026 A | 6/1997 | Hubin et al. |
| 5,680,054 A | 10/1997 | Gauthier |
| 5,698,977 A | 12/1997 | Fulton et al. |
| 5,719,771 A | 2/1998 | Buck et al. |
| 5,721,685 A | 2/1998 | Brown et al. |
| 5,743,495 A | 4/1998 | Ali et al. |
| 5,751,144 A | 5/1998 | Weischedel |
| 5,769,364 A | 6/1998 | Cipollone |
| 5,777,891 A | 7/1998 | Mackay et al. |
| 5,786,535 A | 7/1998 | Ishiyama et al. |
| 5,786,750 A | 7/1998 | Cooper |
| 5,791,063 A | 8/1998 | Gamble et al. |
| 5,798,983 A * | 8/1998 | Kuhn ................... H04B 11/00 367/127 |
| 5,804,731 A | 9/1998 | Jaeggi |
| 5,867,404 A | 2/1999 | Bryan |
| 5,924,654 A | 7/1999 | Anderson |
| 5,956,664 A | 9/1999 | Bryan |
| 5,970,438 A | 10/1999 | Boyle et al. |
| 5,986,547 A | 11/1999 | Boedigheimer et al. |
| 5,987,979 A | 11/1999 | Bryan |
| 5,992,241 A | 11/1999 | Beli et al. |
| 6,026,687 A | 2/2000 | Jury |
| 6,044,698 A | 4/2000 | Bryan |
| 6,055,862 A | 5/2000 | Martens |
| 6,064,428 A | 5/2000 | Cunningham et al. |
| 6,102,340 A | 8/2000 | Basta et al. |
| 6,119,353 A | 9/2000 | Grønskov |
| 6,262,573 B1 | 7/2001 | Wojnarowski et al. |
| 6,324,912 B1 | 12/2001 | Wooh |
| 6,347,265 B1 | 2/2002 | Bidaud |
| 6,349,653 B1 | 2/2002 | Siedlarczyk |
| 6,356,299 B1 | 3/2002 | Trosino et al. |
| 6,373,403 B1 | 4/2002 | Korver et al. |
| 6,405,141 B1 | 6/2002 | Carr et al. |
| 6,415,522 B1 | 7/2002 | Ganz |
| 6,416,020 B1 | 7/2002 | Gronskov |
| 6,417,765 B1 | 7/2002 | Capanna |
| 6,476,603 B2 | 11/2002 | Clark et al. |
| 6,499,339 B1 | 12/2002 | Hedstrom |
| 6,515,249 B1 | 2/2003 | Valley et al. |
| 6,516,668 B2 | 2/2003 | Havira et al. |
| 6,525,658 B2 | 2/2003 | Streetman et al. |

(56) References Cited

U.S. PATENT DOCUMENTS

| | | |
|---|---|---|
| 6,540,180 B2 | 4/2003 | Anderson |
| 6,549,005 B1 | 4/2003 | Hay et al. |
| 6,553,838 B2 | 4/2003 | Amini |
| 6,556,945 B1 | 4/2003 | Burggraf et al. |
| 6,570,497 B2 | 5/2003 | Puckette, IV et al. |
| 6,571,636 B1 | 6/2003 | McWhorter |
| 6,588,114 B1 | 7/2003 | Daigle |
| 6,594,591 B2 | 7/2003 | Clark et al. |
| 6,600,999 B2 | 7/2003 | Clark et al. |
| 6,604,421 B1 | 8/2003 | Li |
| 6,634,112 B2 | 10/2003 | Carr et al. |
| 6,647,891 B2 | 11/2003 | Holmes et al. |
| 6,655,639 B2 | 12/2003 | Grappone |
| 6,681,160 B2 | 1/2004 | Bidaud |
| 6,715,354 B2 | 4/2004 | Wooh |
| 6,725,782 B1 | 4/2004 | Bloom et al. |
| 6,728,515 B1 | 4/2004 | Wooh |
| 6,742,392 B2 | 6/2004 | Gilmore et al. |
| 6,768,298 B2 | 7/2004 | Katragadda et al. |
| 6,778,284 B2 | 8/2004 | Casagrande |
| 6,779,761 B2 | 8/2004 | Holgate |
| 6,830,224 B2 | 12/2004 | Lewin et al. |
| 6,833,554 B2 | 12/2004 | Wooh |
| 6,845,953 B2 | 1/2005 | Hickenlooper et al. |
| 6,854,333 B2 | 2/2005 | Wooh |
| 6,895,362 B2 | 5/2005 | Davenport et al. |
| 6,945,114 B2 | 9/2005 | Cerniglia et al. |
| 6,951,132 B2 | 10/2005 | Batzinger et al. |
| 6,964,202 B2 | 11/2005 | Buttle et al. |
| 6,976,324 B2 | 12/2005 | Lichtberger et al. |
| 6,995,556 B2 | 2/2006 | Carr et al. |
| 7,007,561 B1 | 3/2006 | Conneally et al. |
| 7,023,539 B2 | 4/2006 | Kowalski |
| 7,036,232 B2 | 5/2006 | Casagrande |
| 7,036,774 B2 | 5/2006 | Hickenlooper et al. |
| 7,050,926 B2 | 5/2006 | Lichtberger et al. |
| 7,053,606 B2 | 5/2006 | Buttle et al. |
| 7,054,762 B2 | 5/2006 | Norris et al. |
| 7,081,824 B2 | 7/2006 | Gilbert |
| 7,082,881 B2 | 8/2006 | Bloom et al. |
| 7,152,330 B2 | 12/2006 | Kleeberg |
| 7,164,975 B2 | 1/2007 | Bidaud |
| 7,181,851 B2 | 2/2007 | Lichtberger et al. |
| 7,197,932 B2 | 4/2007 | Morisada et al. |
| 7,226,021 B1 | 6/2007 | Anderson et al. |
| 7,228,747 B2 | 6/2007 | Pieper |
| 7,263,886 B2 | 9/2007 | Jury |
| 7,268,565 B2 | 9/2007 | Anderson |
| 7,270,018 B2 | 9/2007 | Conneally et al. |
| 7,296,770 B2 | 11/2007 | Franke |
| 7,305,885 B2 | 12/2007 | Barshinger et al. |
| 7,311,010 B2 | 12/2007 | Otto et al. |
| 7,312,607 B2 | 12/2007 | Nygaard |
| 7,337,682 B2 | 3/2008 | Conneally et al. |
| 7,392,117 B1 | 6/2008 | Bilodeau et al. |
| 7,394,553 B2 | 7/2008 | Carr et al. |
| 7,403,296 B2 | 7/2008 | Arnold et al. |
| 5,756,903 A1 | 11/2008 | Conneally et al. |
| 7,451,632 B1 | 11/2008 | Conneally et al. |
| 7,463,348 B2 | 12/2008 | Chung |
| 7,502,670 B2 | 3/2009 | Harrison |
| 7,520,415 B2 | 4/2009 | Coomer et al. |
| 7,539,596 B2 | 5/2009 | Luke et al. |
| 7,575,201 B2 | 8/2009 | Bartonek |
| 7,616,329 B2 | 11/2009 | Nagle et al. |
| 7,659,972 B2 | 2/2010 | Magnus et al. |
| 7,698,028 B1 | 4/2010 | Bilodeau et al. |
| 7,716,010 B2 | 5/2010 | Pelletier |
| 7,752,913 B2 | 7/2010 | Brekow et al. |
| 7,755,660 B2 | 7/2010 | Carr et al. |
| 7,755,774 B2 | 7/2010 | Arnold et al. |
| 7,823,841 B2 | 11/2010 | Andarawis et al. |
| 7,849,748 B2 | 12/2010 | Havira |
| 7,869,909 B2 | 1/2011 | Harrison |
| 7,872,736 B2 | 1/2011 | Kanellopoulos et al. |
| 7,882,742 B1 | 2/2011 | Martens |
| 7,920,984 B2 | 4/2011 | Farritor |
| 7,937,246 B2 | 5/2011 | Farritor et al. |
| 7,938,370 B1 | 5/2011 | Franckart et al. |
| 7,940,389 B2 | 5/2011 | Kanellopoulos et al. |
| 7,954,770 B2 | 6/2011 | Fries et al. |
| 7,999,848 B2 | 8/2011 | Chew |
| 8,020,446 B2 | 9/2011 | Bestebreurtje |
| 8,037,763 B2 | 10/2011 | Brignac et al. |
| 8,081,320 B2 | 12/2011 | Nagle et al. |
| 8,125,219 B2 | 2/2012 | Jungbluth et al. |
| 9,108,640 B2 | 8/2015 | Jackson |
| 2001/0019263 A1 | 9/2001 | Kwun et al. |
| 2001/0045495 A1 | 11/2001 | Olson et al. |
| 2002/0113170 A1 | 8/2002 | Grappone |
| 2002/0148931 A1 | 10/2002 | Anderson |
| 2003/0020469 A1 | 1/2003 | Earnest et al. |
| 2003/0070492 A1 | 4/2003 | Buttle et al. |
| 2003/0128030 A1 | 7/2003 | Hintze et al. |
| 2004/0095135 A1 | 5/2004 | Carr et al. |
| 2004/0105608 A1 | 6/2004 | Sloman |
| 2006/0098843 A1 | 5/2006 | Chew |
| 2007/0132463 A1 | 6/2007 | Anderson |
| 2007/0145982 A1 | 6/2007 | Anderson et al. |
| 2007/0163352 A1 | 7/2007 | Bardenshtein et al. |
| 2007/0217670 A1 | 9/2007 | Bar-Am |
| 2008/0105791 A1 | 5/2008 | Karg |
| 2008/0201089 A1 | 8/2008 | Carr et al. |
| 2008/0296441 A1 | 12/2008 | Andarawis et al. |
| 2009/0132179 A1 | 5/2009 | Fu et al. |
| 2009/0266166 A1 | 10/2009 | Pagano |
| 2009/0266167 A1 | 10/2009 | Pagano |
| 2009/0282923 A1 | 11/2009 | Havira |
| 2009/0320603 A1 | 12/2009 | Crocker et al. |
| 2010/0207620 A1 | 8/2010 | Gies |
| 2010/0312493 A1 | 12/2010 | Chen et al. |
| 2011/0006167 A1 | 1/2011 | Tolmei |
| 2011/0043199 A1 | 2/2011 | Crocker |
| 2011/0199607 A1 | 8/2011 | Kanellopoulos et al. |
| 2011/0216996 A1 | 9/2011 | Rogers |
| 2011/0233293 A1 | 9/2011 | Kral et al. |
| 2011/0255077 A1 | 10/2011 | Rogers |
| 2011/0276203 A1 | 11/2011 | Hase |
| 2013/0082857 A1* | 4/2013 | Beer ..................... G01S 13/90 342/22 |
| 2013/0151133 A1* | 6/2013 | Kickbusch .......... B61L 27/0027 701/117 |
| 2013/0169037 A1 | 7/2013 | Bieg et al. |
| 2014/0041980 A1 | 2/2014 | Noffsinger et al. |
| 2014/0046513 A1* | 2/2014 | Cooper ................. B61L 23/042 701/20 |
| 2014/0129060 A1* | 5/2014 | Cooper ............... B61L 15/0027 701/19 |
| 2014/0129154 A1* | 5/2014 | Cooper ................. B61L 3/121 702/34 |
| 2015/0053827 A1* | 2/2015 | Noffsinger ............. B61L 3/10 246/121 |

FOREIGN PATENT DOCUMENTS

| | | |
|---|---|---|
| DE | 102010045234 A1 | 3/2012 |
| WO | 9530886 | 11/1995 |
| WO | 9601431 | 1/1996 |
| WO | 0009377 | 2/2000 |
| WO | 0230729 | 4/2002 |
| WO | 02060738 | 8/2002 |
| WO | 2007110613 | 10/2007 |
| WO | 2008012535 | 1/2008 |
| WO | 2008099177 | 8/2008 |
| WO | 2009087385 | 7/2009 |

(56) References Cited

FOREIGN PATENT DOCUMENTS

| | | |
|---|---|---|
| WO | 2011146088 | 11/2011 |
| WO | 2012041978 A2 | 4/2012 |

OTHER PUBLICATIONS

Aharoni, R.; Glikman, Eli; "A Novel high-speed rail inspection system", ScanMaster Systems (IRT) Ltd., Oct. 2002, vol. 7, No. 10, 8 pgs.

http://www.progressiverailroading.com/mow/article/Maintenance-of-Way-Track-inspection, "Maintenance of Way: Track inspection technology", 7 pgs.

Rose, J.L.; Avioli, M.J.; Song, W.J., "Application and potential of guided wave rail inspection", Insight vol. 44, No, 6., Jun. 2002, 6 pgs.

Sperry Rail Service, Sperry B-Scan Dual Rail Inspection System, For superior technology, training, and reporting, the solution is Sperry, 4 pgs.

Hocking, Rail Inspection, The Eddy Current Solution, 17 pgs.

Innotrack, Project No. TIP5-CT-2006-031415, 43 pgs.

\* cited by examiner

SYSTEM AND METHOD FOR ACOUSTICALLY IDENTIFYING DAMAGED SECTIONS OF A ROUTE

FIELD

Embodiments of the subject matter described herein relate to examining routes traveled by vehicles for damage to the routes.

BACKGROUND

Routes that are traveled by vehicles may become damaged over time with extended use. For example, tracks on which rail vehicles travel may become damaged and/or broken. A variety of known systems are used to examine rail tracks to identify where the damaged and/or broken portions of the track are located. For example, some systems use cameras, lasers, and the like, to optically detect breaks and damage to the tracks. The cameras and lasers may be mounted on the rail vehicles, but the accuracy of the cameras and lasers may be limited by the speed at which the rail vehicles move during inspection of the route. As a result, the cameras and lasers may not be able to be used during regular operation (e.g., travel) of the rail vehicles in revenue service.

Other systems use ultrasonic transducers that are placed at or near the tracks to ultrasonically inspect the tracks. These systems may require very slow movement of the transducers relative to the tracks in order to detect damage to the track. When a suspect location is found by ultrasonic inspection, a follow-up manual inspection may be required for confirmation of potential defects using transducers that are manually positioned and moved along the track and/or are moved along the track by a relatively slower moving inspection vehicle. Inspections of the track can take a considerable amount of time, during which the inspected section of the route may be unusable by regular route traffic.

Other systems use wayside devices that send electric signals through the tracks. If the signals are not received by other wayside devices, then a circuit that includes the track is identified as being open and the track is considered to be broken. These systems are limited at least in that the wayside devices are immobile. As a result, the systems cannot inspect large spans of track and/or a large number of devices must be installed in order to inspect the large spans of track.

Other systems use human inspectors who move along the track to inspect for broken and/or damaged sections of track. This manual inspection is slow and prone to errors.

BRIEF DESCRIPTION

In an embodiment, a method (e.g., for acoustically examining a route) includes sensing passively excited residual sounds of a vehicle system during travel over a route, examining the passively excited residual sounds to identify one or more changes of interest in the passively excited residual sounds, and identifying a section of the route as being damaged responsive to the one or more changes of interest in the passively excited residual sounds that are identified.

In an embodiment, a system (e.g., for acoustically examining a route) includes a deviation detection device and an identification device. The deviation detection device is configured to receive passively excited residual sounds of a vehicle system sensed by one or more acoustic pickup devices during travel over a route. The deviation detection device also is configured to examine the passively excited residual sounds to identify one or more changes of interest in the passively excited residual sounds. The identification device is configured to identify a section of the route as being damaged responsive to the one or more changes of interest in the passively excited residual sounds that are identified by the deviation detection device.

In an embodiment, a method (e.g., for examining a route) includes generating an acoustical signature of audible passively excited residual sounds generated by movement of a vehicle system along a route, examining one or more subsets of frequencies of the audible passively excited residual sounds in the acoustical signature to identify one or more changes of interest, and identifying a section of the route as being damaged using the one or more changes of interest.

BRIEF DESCRIPTION OF THE DRAWINGS

The subject matter described herein will be better understood from reading the following description of non-limiting embodiments, with reference to the attached drawings, wherein below.

DETAILED DESCRIPTION

Figure 1:
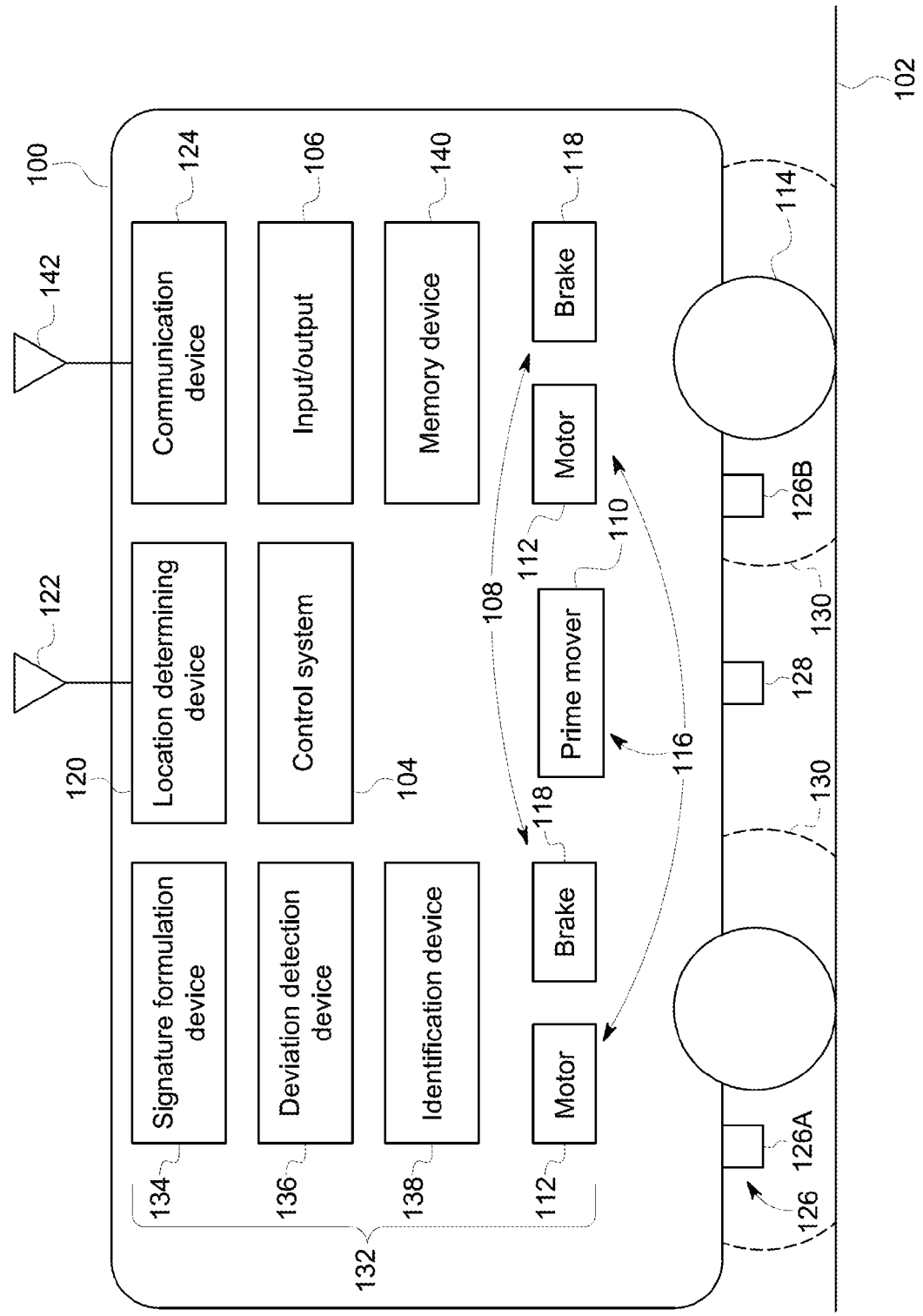
FIG. 1 is a schematic illustration of an embodiment of a vehicle system.

Embodiments of the inventive subject matter described herein relate to monitoring sounds during travel of a vehicle system along a route in order to identify and/or confirm damaged sections of the route. The term "vehicle system" can refer to a single vehicle (e.g., a locomotive, an automobile, an off-highway vehicle that is not designed or permitted for travel on public roads, or the like) or a combination of two or more vehicles that are mechanically coupled with each other to travel along the route (e.g., a vehicle consist such as a rail vehicle consist or train).

The sounds that are monitored may be passively excited sounds. For example, the sounds may not be created or generated by a device for the primary or sole purpose of generating acoustic waves. The sounds may be residual noises that occur during travel and operation of the vehicle system. As some examples, the residual noises may be created by the movement of wheels of the vehicle system along the route (e.g., rails of a track, road, ground, or the like), operation of a prime mover (e.g., engine and/or generator/alternator) of the vehicle system, operation of a motor (e.g., traction motor) of the vehicle system, vibrations of the vehicle system caused by movement of the vehicle system, or the like. In one aspect, the noise excitation is primarily from the prime mover and electrical machines of the vehicle system, combined with wheel to route dynamics (e.g., engagement and/or movement of the wheel to the route).

The sounds may be audible to a human being of average abilities, such as those sounds having frequencies in the range of 20 Hertz to 20,000 Hertz. The sounds may not include ultrasonic sounds, such as ultrasonic waves that are directed toward or injected into the route. The sounds may be passively excited in that the sounds occur as a natural outcome from operation of the vehicle system. For example, the vehicle system may not be able to operate to travel down the route without generating the passively excited sounds. The passively excited sounds may not be generated for being directed into the route for examination purposes. For example, the passively excited sounds that are monitored do not include ultrasound waves that are directed into a rail to examine the structural integrity of the rail in one embodiment.

The passively excited sounds are detected to generate acoustic signatures of these sounds as the vehicle system travels along the route. The acoustic signatures may be frequency spectra of the detected residual noises that represent the residual noises that are detected at one or more points in time. The signatures optionally may represent these noises in another domain, such as time. The system and method may operate to detect changes of interest (e.g., deviations) in the acoustic signature. These changes of interest can include a step change (such as an absence of one or more residual noises), a tonal change (e.g., a detected tone or sound of a designated frequency), a frequency change (e.g., a relatively significant decrease or increase in the frequencies in the signature), a decibel change (e.g., a relatively significant increase or decrease in the decibel level of the sounds), or another change.

One or more acoustic pickup devices (e.g., microphones or other acoustic detectors) can be positioned outside of the vehicle system to detect the passively excited residual sounds. The system and method may examine an entire frequency spectrum (or other domain spectrum) of an acoustic signature representative of the detected sounds, or may examine only a subset or portion of the signature to determine if a change of interest occurs in the signature. For example, only a relatively small band of frequencies may be examined to determine if a change of interest occurs within the band of frequencies.

The sensed noises can be referenced to vehicular control events. For example, throttle settings, brake settings, accelerations (including decelerations as negative accelerations), speeds, ON or OFF states of motors, and the like, may be temporally correlated or matched to different portions or times of the acoustic signature. This correlation or matching can be used to eliminate some changes in the acoustic signature from being identified as changes of interest representative of damaged sections of the route. As one example, if the vehicle system is a rail vehicle traveling over a track that is divided into segments separated by relatively small gaps, changes in the acoustic signature can be correlated to the speed at which the rail vehicle is traveling so that the changes in the acoustic signature that occur at a rate that matches or corresponds to the speed at which the rail vehicle is moving may be associated with the gaps between the segments of the rail, as opposed to being identified as broken sections of the rail.

The acoustic pickup devices can be disposed outside the vehicle system within a target measurement area. The target measurement area may be a volume of space around the location where a wheel or other part of the vehicle system that moves along the route to propel the vehicle system engages the route. For example, the acoustic pickup devices may be positioned within a few centimeters to a meter (or another distance) from the wheels of a rail vehicle. In one aspect, one or more background acoustic pickup devices may be positioned outside the target measurement area. These background pickup devices can detect passively excited residual sounds other than those generated by movement of the wheel along the route. These sounds can be referred to as background noise. The background noise may be compared to or subtracted from the acoustic signature to eliminate the background noise from examination when attempting to determine if the sounds of the wheels moving along the route indicate damage to the route.

Different types of damage to the route can be associated with different changes of interest or different acoustic signatures. For example, a first change of interest or first acoustic signature may be associated with a rail that is broken through an entirety of a cross-section of the rail. A different, second change of interest or different, second acoustic signature may be associated with a rail that is broken through no more than half of the cross-section of the rail. A different, third change of interest or different, third acoustic signature may be associated with a rail that is cracked, but not broken through a significant portion of the cross-section of the rail. These changes of interest or acoustic signatures can be obtained from empirical studies, such as by having the vehicle system travel over different types of routes having known damaged sections. The acoustic signatures and changes of interest that are detected during these travels can be stored in a memory device and then compared to actual acoustic signatures or changes of interest sensed during travel of the vehicle system over a route having unknown or unidentified damaged sections. The actual acoustic signatures or changes of interest can be compared to the stored acoustic signatures or changes of interest. If the actual signatures or changes match (e.g., within a designated confidence range) the stored signatures or changes, then the damage in the route that is actually detected may be identified as the same type or category of damage to the route that is associated with the matching stored signature or change.

Use of the passively excited residual sounds to detect damaged sections of a route can allow the vehicle system to examine the route with fewer restrictions than some known systems and methods. For example, the vehicle system may travel at relatively fast speeds while examining the passively excited residual sounds, such as while traveling at the speed limit (e.g., track speed) of the route or another relatively fast speed (e.g., 70 miles per hour or 112 kilometers per hour). The use of the passively excited residual sounds to detect damaged route sections also may provide a more reliable testing system and method, as the system and method may only involve acoustic sensors (e.g., pickup devices) that detect the passively excited residual sounds and software systems that analyze these sounds. Other known systems and methods (e.g., ultrasound inspection systems and methods) may require generation and steering of ultrasound waves into the route (e.g., rail) while being engaged with the route, and detection of echoes of these waves. The generation of ultrasound waves can require additional equipment that may provide another source of failure for the system and method.

FIG. 1 is a schematic illustration of an embodiment of a vehicle system 100. The vehicle system 100 may represent a propulsion-generating vehicle that is capable of generating tractive effort to propel the vehicle system 100 along a route 102. For example, the vehicle system 100 may represent a rail vehicle (e.g., a locomotive), another off-highway vehicle (e.g., a vehicle that is not designed or permitted for travel on public roadways), an automobile, or another type of vehicle. Optionally, the vehicle system 100 may represent multiple vehicles mechanically connected together. For example, the vehicle system 100 may include the vehicle shown in FIG. 1 coupled with one or more other propulsion-generating vehicles and/or one or more non-propulsion-generating vehicles (e.g., railcars) for traveling together along the route 102, such as in a vehicle consist or rail vehicle consist.

The vehicle system 100 includes several components that operate to control the vehicle system 100 and/or to monitor the passively excited residual sounds in order to identify and/or confirm damaged sections of the route 102. These components may communicate with each other via wired and/or wireless connections.

A control system 104 of the vehicle system 100 controls operations of the vehicle system 100. The control system 104 may include or represent one or more onboard and/or off-board processors, controllers, or other logic based devices (and/or associated hardware, circuitry, and/or software stored on a tangible and non-transitory computer readable medium or memory). The control system 104 may communicate with one or more operator input and/or output devices 106 ("Input/Output" in FIG. 1) in order to communicate with an operator of the vehicle system 100. The control system 104 may receive manually input commands to control the tractive efforts and/or braking efforts generated by a respective one of a propulsion system 116 and a braking system 108 of the vehicle system 100. The propulsion system 116 includes a prime mover 110 (e.g., an engine and/or generator/alternator) that generates electric current for powering one or more motors 112 (e.g., traction motors) coupled with axles and/or wheels 114 of the vehicle system 100. The powered motors 112 rotate the axles and/or wheels 114 to propel the vehicle system 100. Optionally, the prime mover 110 may represent an onboard energy storage device (e.g., a battery), connections with an off-board power supply (e.g., a catenary, conductive shoe that engages a powered rail, or the like), or another mechanism capable of powering the motors 112 to propel the vehicle system 100. The braking system 108 includes brakes 118, such as airbrakes, dynamic brakes, or the like, that generate braking effort to slow or stop movement of the vehicle system 100.

The input/output device 106 may be used by an operator to control the monitoring of passively excited residual noise for detection of damage to the route 102 and/or for reporting the detection of a damaged section of the route 102 from the passively excited residual noise. The input/output device 106 can include one or more monitors, displays, keyboards, touchscreens, speakers, microphones, and the like.

A location determining device 120 operates to receive signals from one or more off-board sources that represent locations and/or headings of the vehicle system 100. For example, the location determining device 120 may include a receiver, antenna 122, and associated circuitry for receiving wireless signals representative of the location and/or heading of the vehicle system 100. The signals may be received from satellites (e.g., GPS signals received from GPS satellites), from wayside devices, from other vehicle systems, from cellular towers or stations, from transponders disposed alongside the route 102, from RFID tags disposed alongside the route 102, and the like. The location determining device 120 and/or the control system 102 can determine the location of the vehicle system 100 from the received signals.

A communication device 124 of the vehicle system 100 communicates with other vehicles and/or other remote locations that are off-board the vehicle system 100. The communication device 124 may include or represent an antenna 142 (along with associated transceiver hardware circuitry and/or software applications) for wirelessly communicating with other vehicles and/or remote locations. Optionally, the communication device 124 may communicate via one or more wired connections, such as a multiple unit (MU) cable, a trainline, an electrically controlled pneumatic (ECP) brake line, and the like.

The vehicle system 100 includes a memory device 140 that may include or represent one or more memories (e.g., a tangible and non-transitory computer readable memory, such as a computer hard drive, EEPROM, ROM, RAM, or the like) having a table, list, database, or other memory structure used to store information used in conjunction with performing one or more of the methods described herein.

The vehicle system 100 includes one or more acoustic pickup devices 126 (e.g., 126A, 126B), 128. The acoustic pickup devices 126, 128 represent acoustic sensors that are capable of detecting sounds, such as the passively excited residual sounds, during travel of the vehicle system 100. In one aspect, the pickup devices 126, 128 can include microphones, piezoelectric transducers that convert received acoustic waves into electric signals, or the like. The pickup devices 126, 128 can generate (e.g., autonomously generate) these electric signals upon detection of the sounds or as the sounds are detected.

The pickup devices 126, 128 may be air coupled acoustic pickup devices that detect audible sounds. By "air coupled," it is meant that the pickup devices 126, 128 may be spaced apart from the wheels 114 and/or route 102, and may not directly engage the wheels 114 or route 102 and/or may not be coupled or interconnected to the wheels 114 or route 102 by another, non-air component. For example, the pickup devices 126, 128 may not directly engage or contact the route 102, and may not be interconnected with the route 102 by acoustically transmissive gels or other materials used in ultrasound applications, for example.

The pickup devices 126 are disposed within target measurement areas 130 of the vehicle system 100. The target measurement areas 130 represent volumes of space around a location where the vehicle system 100 engages the route 102. For example, the target measurement areas 130 may include the space that is close enough for the pickup devices 126 to record the sounds generated by the wheels 114 engaging and moving along the route 102. The size of the target measurement areas 130 may vary depending on the acoustic sensitivity of the pickup devices 126. For less sensitive pickup devices 126, the target measurement area 130 may be smaller. For more sensitive pickup devices 126, the target measurement area 130 may be larger. In one aspect, the target measurement area 130 is sufficiently small that the area 130 is associated with a single wheel 114 and the pickup device 126 disposed within that area 130 senses the noises generated by engagement of that wheel 114 with the route 102, and not the noises generated by another wheel 114 in another target measurement area 130.

A single pickup device 126 may be used with the vehicle system 100. For example, a single microphone may be used to detect the passively excited residual sounds that are used to identify damaged sections of the route 102. Optionally, several pickup devices 126 may be used. For example, a pickup device 126 may be provided for each wheel 114 of the vehicle system 100. With respect to rail vehicles, several pickup devices 126 may be located such that the pickup devices 126 detect the sounds generated by the wheels 114 rolling along the same rail of the route 102.

The pickup device 128 is disposed outside of the target measurement areas 130 of the wheels 114. This pickup device 128 may be referred to as a background acoustic pickup device 128. The pickup device 128 detects the passively excited residual sounds other than the sounds generated by the wheels 114 moving along the route 102. For example, the pickup device 128 may sense the background noises generated by operation of the propulsion system, the braking system, the wind, urban noises, or the like.

The vehicle system 100 includes a route damage detection system 132 that monitors the passively excited residual sounds sensed by the pickup devices 126 and/or 128 during travel of the vehicle system 100, determines acoustic signatures of these residual sounds, identifies changes of interest in the acoustic signatures, and/or identifies damaged sections of the route 102 from these changes of interest. Although all components of the detection system 132 are shown in FIG. 1 as being disposed onboard the vehicle system 100, one or more of these components may be disposed off-board the vehicle system 100. Such off-board components may communicate with the onboard components via the communication device.

The detection system 132 includes a signature formulation device 134. The formulation device 134 includes or represents one or more onboard and/or off-board processors, controllers, or other logic based devices (and/or associated hardware, circuitry, and/or software stored on a tangible and non-transitory computer readable medium or memory). The formulation device 134 receives the passively excited residual sounds from the pickup devices 126, 128 and generates one or more acoustic signatures from the residual sounds.

Figure 2:
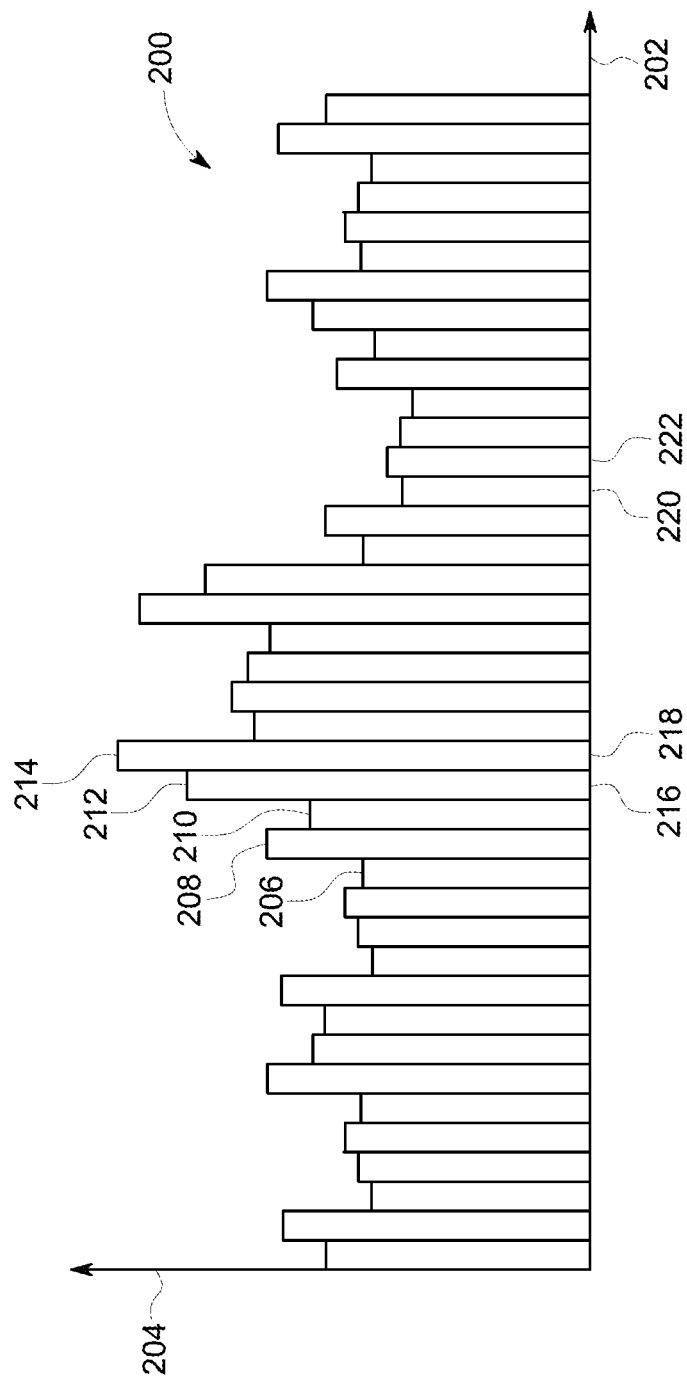
FIG. 2 illustrates an example of an acoustic signature of passively excited residual sounds during travel of the vehicle system shown in FIG. 1 along a route.

With continued reference to FIG. 1, FIG. 2 illustrates an example of an acoustic signature 200 of passively excited residual sounds during travel of the vehicle system 100 along the route 102. The acoustic signature 200 is shown alongside a horizontal axis 202 representative of frequencies of the residual sounds and a vertical axis 204 representative of magnitudes (e.g., decibels) of the residual sounds. Optionally, the acoustic signature 200 may not be in the frequency domain (as shown in FIG. 2), but may be in another domain, such as the time domain.

The acoustic signature 200 may represent the sounds detected by one of the pickup devices 126, or may represent the sounds detected by plural (or all) of the pickup devices 126. Due to changes in various residual sounds during movement of the vehicle system 100, the acoustic signature 200 may change in one or more frequencies over time. For example, one or more peaks 202 in the signature 200 may increase or decrease at a later time, indicating that the sounds associated with those peaks are louder or quieter (or not detected).

The signature formulation device 134 can form the acoustic signature 200 from a comparison of the residual sounds detected by one or more of the pickup devices 126 and the residual sounds detected by the background pickup device 128. For example, the signature formulation device 134 can remove (e.g., subtract out) the residual sounds detected by the background pickup device 128 from the residual sounds detected by the pickup device 126A for the acoustic signature 200 that is generated for the pickup device 126A. Removing the background residual noises detected by the background pickup device 128 from the residual sounds detected by the pickup device 126A can result in the acoustic signature 200 being more representative of the residual sounds generated by movement of the wheel 114 (that has the target measurement area 130 that includes the pickup device 126A) along the route 102 than if the background residual noises were not removed.

The acoustic signature 200 may represent the residual noises of the vehicle system 100 at one time, with one or more other acoustic signatures representing the residual noises at other times. One or more frequencies of the acoustic signature 200 may vary over time. For example, peaks 206, 208, 210 in the acoustic signature 200 may decrease when the wheel 114 that creates at least some of the residual noises represented by the signature 200 passes over a regular gap in segments of a rail. The decrease in the peaks 206, 208, 210 can be due to a reduced residual noise resulting from the wheel 114 passing over the gap.

Optionally, the signature formulation device 134 may create the acoustic signature 200 as an average, median, or other statistical measure of the residual sounds that are sensed over a period of time. For example, the acoustic signature 200 may represent an average of the decibels of the frequencies of the residual sounds detected by one or more of the pickup devices 126 over the previous 30 seconds, minute, two minutes, four minutes, thirty minutes, or another time period. In such an example, the acoustic signature 200 can represent an average, median, or other measure of the residual sounds over a moving window of time.

A deviation detection device 136 of the detection system 132 examines the acoustic signature 200 generated by the formulation device 134 for one or more changes of interest in the acoustic signature 200. The changes of interest represent relatively significant changes in one or more frequencies of the acoustic signature 200 at one or more points in time that are caused by one or more wheels 114 of the vehicle system 100 striking over and/or traveling over a damaged section of the route 102. For example, when a wheel 114 travels over a break through the entire cross-section of the route 102, there may be a decrease or elimination of one or more frequencies in the acoustic signature 200. As another example, when the wheel 114 travels over a partial break through less than the entire cross-section of the route 102, there may be a decrease, but not elimination, of one or more frequencies in the acoustic signature 200. In another example, when the wheel 114 travels over a portion of the route 102 that is bent or otherwise misshaped (e.g., such as when the two parallel sections of the route 102 are closer together than the lateral spacing between the wheels 114 of the vehicle system 100), the wheel 114 may generate a higher pitched ringing or other sound. As a result, one or more frequencies in the acoustic signature 200 may increase.

Figure 3:
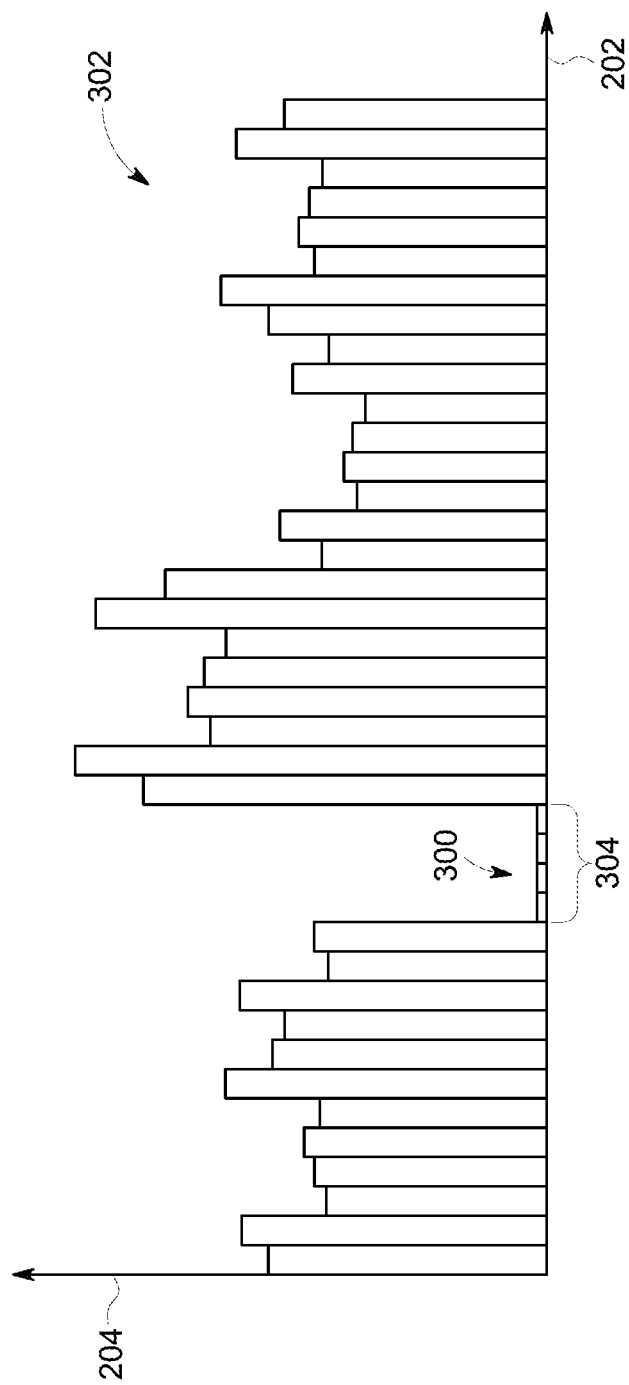
FIG. 3 illustrates an example of a step change in an acoustic signature.
Figure 4:
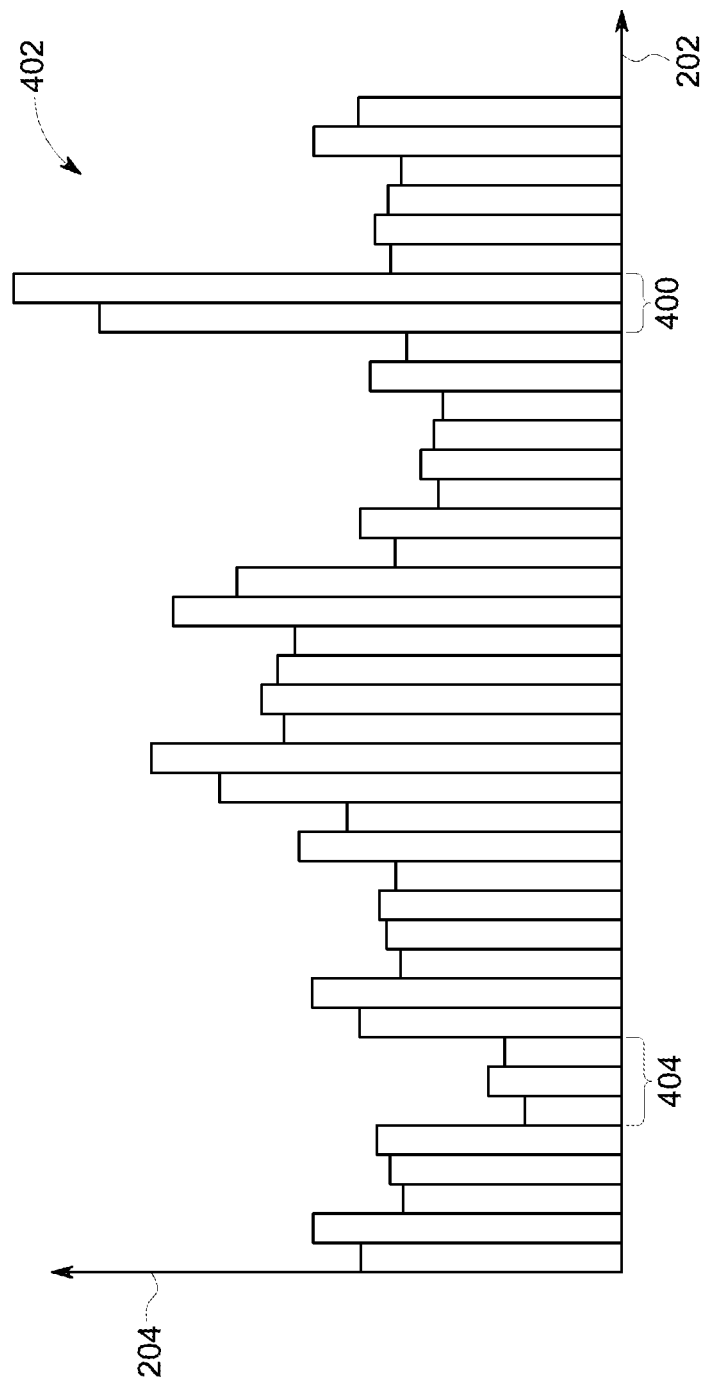
FIG. 4 illustrates examples of tonal changes in an acoustic signature.
Figure 5:
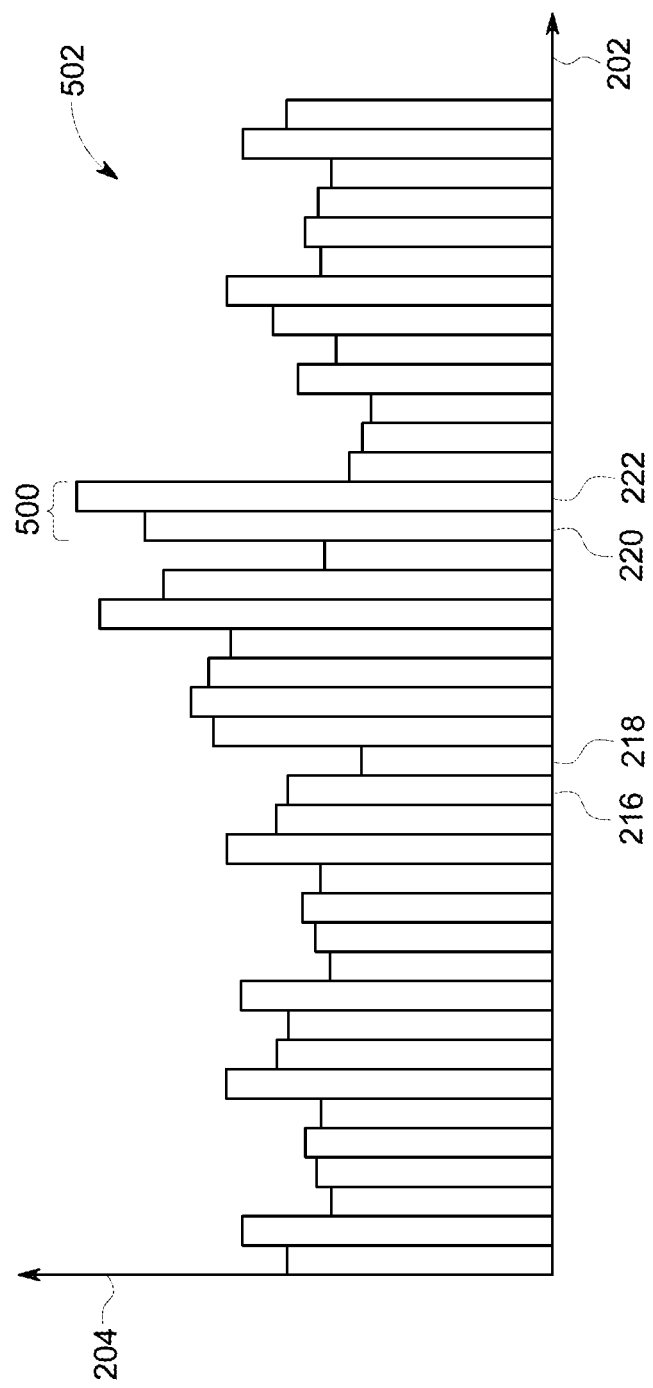
FIG. 5 illustrates examples of a frequency change in an acoustic signature.

FIGS. 3 through 5 illustrate examples of different changes of interest that may be identified by the detection device 136 shown in FIG. 1. FIG. 3 illustrates an example of a step change 300 in an acoustic signature 302. The acoustic signature 302 may be similar to the acoustic signature 200 shown in FIG. 2. For example, the acoustic signature 302 also is shown alongside the horizontal and vertical axes 202, 204, and represents the magnitudes of various frequencies of residual sounds detected by one or more of the pickup devices 126. The acoustic signature 200 may represent the residual sounds sensed at an earlier point in time or over an earlier period of time, and the acoustic signature 302 may represent the residual sounds sensed at a later point in time or over a later period of time.

As shown in a comparison of the acoustic signatures 200, 302, the magnitude of the residual sounds within a frequency range 304 are significantly reduced or eliminated. This reduction or elimination represents the step change 302. The detection device 136 may detect the step change 302 when the magnitude (e.g., decibels) of frequencies (e.g., a range of a designated number of frequencies) decreases by at least a designated threshold and/or is eliminated (or substantially eliminated). For example, when at least a 5 Hertz band of frequencies (or another amount of the frequencies) in the acoustic signature 200 decreases by at least 75% (or another amount) or is eliminated (as shown in FIG. 3), then the detection device 136 may identify the step change 300.

FIG. 4 illustrates examples of tonal changes 400, 404 in an acoustic signature 402. A tonal change 400, 404 also may be referred to as a decibel change. The acoustic signature 402 may be similar to the acoustic signature 200 shown in FIG. 2.

For example, the acoustic signature 402 also is shown alongside the horizontal and vertical axes 202, 204, and represents the magnitudes of various frequencies of residual sounds detected by one or more of the pickup devices 126. The acoustic signature 200 may represent the residual sounds sensed at an earlier point in time or over an earlier period of time, and the acoustic signature 402 may represent the residual sounds sensed at a later point in time or over a later period of time.

The tonal changes 400, 404 represent changes in tones in the acoustic signature 200. For example, when the decibel level of one or more designated frequencies associated with a tone (e.g., a high or low pitched ringing sound) increases or decreases, the tone associated with the designated frequencies becomes louder or quieter, respectively. Such a change in the tone represents a tonal or decibel change. In the illustrated example, the tonal change 400 represents a louder tone relative to the acoustic signature 200 while the tonal change 404 represents a quieter tone relative to the acoustic signature 200. Consequently, the higher pitched tone represented by the frequencies in the tonal change 400 may be louder than in the acoustic signature 200 and the lower pitched tone represented by the frequencies in the tonal change 404 may be quieter than in the acoustic signature 200.

The detection device 136 may detect the tonal changes 400, 404 when the magnitude (e.g., decibels) of one or more designated frequencies increase or decrease by designated thresholds. The designated frequencies may be associated with particular types or degrees of damage to the route 102. For example, the lower pitched frequencies associated with the tonal change 404 may be associated with a break in the rail of a route 102, while the higher pitched frequencies associated with the tonal change 400 may be associated with a bend or other change in the shape of the rail of the route 102 that causes the wheels 114 to generate higher pitched, ringing sounds.

The designated frequencies used to detect tonal changes representative of different types and/or degrees of damage to the route 102 may be empirically determined by recording the tonal changes that occur when a vehicle system travels over a route having known types and/or degrees of damage. The frequencies at which the tonal changes occur when the vehicle system 100 passes over the known damaged sections of a route can be recorded and used during later trips of the vehicle system 100 over routes 102 having unknown types and/or degrees of damage.

FIG. 5 illustrates examples of a frequency change 500 in an acoustic signature 502. The acoustic signature 502 may be similar to the acoustic signature 200 shown in FIG. 2. For example, the acoustic signature 502 also is shown alongside the horizontal and vertical axes 202, 204, and represents the magnitudes of various frequencies of residual sounds detected by one or more of the pickup devices 126. The acoustic signature 200 may represent the residual sounds sensed at an earlier point in time or over an earlier period of time, and the acoustic signature 502 may represent the residual sounds sensed at a later point in time or over a later period of time.

The frequency change 500 represents a shift in frequencies (e.g., tone) in the acoustic signature 200. For example, peaks 212, 214 in the acoustic signature 200 occur at frequencies 216, 218. In the acoustic signature 502, however, the peaks 212, 214 have shifted frequencies from the frequencies 216, 218 to higher frequencies 220, 222. Alternatively, the peaks 212, 214 may have shifted to lower frequencies. The shifting of the peaks 212, 214 between frequencies may result from a tone that is generated when the wheels 114 travel over the route 102 changing pitch, such as from a lower pitched sound to a higher pitched sound. The decibel level of the tone may stay the same or substantially the same, but the pitch of the tone may change.

The detection device 136 may detect the frequency change 500 when the decibel level of one or more designated frequencies in the acoustic signature 200 changes, but is the same or substantially the same in one or more other designated frequencies in a later acoustic signature 502. For example, first decibel levels of the frequencies 216, 218 in the signature 200 may decrease to lower second decibel levels in the signature 502, while third decibel levels of the frequencies 220, 222 in the signature 200 increase to the first decibel levels in the signature 502. This shifting of decibel levels between frequencies may be indicative of damage to the route 102.

The above changes of interest are provided as examples. The detection device 136 optionally may identify other changes in frequencies and/or decibels in an acoustic signature as being changes of interest.

In one aspect, the signature formulation device 134 creates an acoustic signature from an average, median, or other statistical measure of the sensed residual sounds over a period of time. Such an acoustic signature may be referred to as a live or real-time acoustic signature because the acoustic signature is formed from the passively excited residual sounds that are sensed by the pickup devices 126 and/or 128 during travel of the vehicle system 100 along the route 102. The detection device 136 may examine changes to such an acoustic signature in order to determine if any of these changes are changes of interest.

Optionally, the acoustic signature 200 may be a designated signature representative of residual sounds that are expected or known to occur when the vehicle system 100 travels over a segment of the route 102 that does not have damaged portions. The vehicle system 100 (or a similar but not the same vehicle system 100) may travel over a route having no damage, little damage, or known damage during one or more empirical test trips, and the residual sounds may be recorded. One or more acoustic signatures of these residual sounds may be created and saved (e.g., on the memory device 124). The acoustic signature 200 may represent such a saved or stored acoustic signature. The detection device 136 may then compare an actual acoustic signature representative of the passively excited residual sounds sensed during actual travel of the vehicle system 100 with the saved acoustic signature in order to identify changes of interest. Optionally, the acoustic signature 200 may represent a mathematical model or assumed spectrum of the residual sounds that are calculated or expected to be experienced by the vehicle system 100 traveling over a route with little to no damage.

In one aspect, the vehicle system 100 may include an acoustic output device that generates audible sounds. For example, the pickup device 128 can include or represent a speaker that creates human audible sounds, such as white noise. These sounds can be sufficiently loud and/or be generated at designated frequencies to drown out the passively excited residual sounds that are not created by the wheels 114 traveling over damaged sections of the route 102. For example, the white noise that is generated can include sounds at the same or similar frequency as noises generated by the propulsion system 116 of the vehicle system 100, but at greater decibel levels. This while noise can drown out changes in the residual sounds generated by the propulsion system 116, such as those that occur when throttle and/or brake settings of the vehicle system 100 change.

The white noise that is generated can cause the acoustic signatures created by the formulation device 134 to exhibit very little to no changes other than changes that are caused by travel over a damaged portion of the route 102. For example, the acoustic signatures may have fewer peaks and valleys than the acoustic signature 200 due to the white noise. When the vehicle system 100 travels over a damaged portion of the route 102, however, one or more peaks in the acoustic signature 200 may increase or decrease to reflect a change of interest. This change of interest may represent travel over the damaged portion of the route 102.

The detection device 136 may change which frequencies in the acoustic signatures are examined for a step change, frequency change, or tonal change indicative of damage to the route 102 based on the size (e.g., mass and/or weight) of the vehicle system 100. For example, for lighter vehicle systems 100, the detection device 136 may examine larger frequencies in the acoustic signatures for step changes, frequency changes, or tonal changes indicative of damage to the route 102 relative to heavier vehicle systems 100. The lighter vehicle systems 100 may cause the passively excited residual sounds generated by the wheels 114 traveling over damaged sections of the route 102 to generate higher pitched tones or sounds. Conversely, for heavier vehicle systems 100, the detection device 136 may examine smaller frequencies in the acoustic signatures for step changes, frequency changes, or tonal changes indicative of damage to the route 102. The heavier vehicle systems 100 may cause the passively excited residual sounds generated by the wheels 114 traveling over damaged sections of the route 102 to generate lower pitched tones or sounds.

The detection device 136 may isolate which portion(s) of the acoustic signatures are being examined to detect changes of interest. The detection device 136 may only examine one or more subsets of the entire frequency spectrum in an acoustic signature in order to determine if a change of interest is present. For example, instead of examining all or a substantial portion of the residual noises having frequencies of 20 Hertz to 20,000 Hertz, the detection device 136 may select a smaller portion of these frequencies to examine.

The subsets of frequencies include designated frequencies that are examined by the detection device 136 to determine if a change of interest occurred may be selected based on a type or category of damage that is sought to be detected by the system 132. For example, a first subset of frequencies may be associated with a first type of damage (e.g., a break through the entire cross-section of a rail in the route 102), a different, second subset of frequencies may be associated with a different, second type of damage (e.g., a crack in the rail), a different, third subset of frequencies may be associated with a different, third type of damage (e.g., pitting in the rail), and so on. The different subsets of frequencies may partially overlap one another or may not overlap one another. The frequencies that are in the various subset The correspondence between the different subsets of frequencies and the different types or categories of damage to the route 102 may be empirically determined. For example, a vehicle system may travel over a route having sections with known types of damage. Acoustic signatures may be created from the passively excited residual sounds, and the subsets of frequencies in these signatures that correspond to the different types of damage may be identified therefrom.

Additionally or alternatively, the detection device 136 may isolate which portion(s) of the acoustic signatures are being examined to detect changes of interest based on the type of vehicle system 100 and/or propulsion system 116 that is traveling along the route 102. Different vehicle systems 100 and/or propulsion systems 116 may generate different sounds during travel along the route 102. For example, a first propulsion system 116 of a first vehicle system 100 may generate lower frequency passively excited residual sounds than a different, second vehicle system 116 of a different, second vehicle system 100. The detection device 136 may examine lower frequencies of acoustic signatures for the first vehicle system 100 and/or first propulsion system 116 than for the second vehicle system 100 and/or second propulsion system 116 in order to ensure that the frequencies associated with potential damage to the route 102 are examined.

The correspondence between the different subsets of frequencies and the different types or categories of vehicle systems 100 and/or propulsion systems 116 may be empirically determined. For example, different vehicle systems having different propulsion systems may travel over a route having sections with known damage. Acoustic signatures may be created from the passively excited residual sounds generated by the different vehicle systems, and the subsets of frequencies in these signatures that correspond to the damaged sections of the route when the different vehicle systems travel over the sections may be identified therefrom.

In one aspect, the detection device 136 may use one or more reference tracking techniques to identify changes of interest in acoustic signatures that are indicative of damage to the route 102. The reference tracking techniques involve temporally matching or correlating changes in the acoustic signatures with vehicle control events. The reference tracking techniques can be used to differentiate between changes of interest in the acoustic signatures that are caused by travel over damaged sections of the route 102 and changes of interest having other causes. The vehicle control events can include, without limitation, speeds, accelerations (including decelerations), throttle settings, brake settings, and the like, of the vehicle system 100.

As one example of a reference tracking technique, the detection device 136 may determine a moving speed of the vehicle system 100 from speed data provided by the control system 104. The control system 104 may include or represent one or more speed sensors, such as tachometers, that generate data indicative of the speed of the vehicle system 100. The control system 104 may report the speed of the vehicle system 100 based off of a throttle and/or brake setting of the input/output device 106. Optionally, the detection device 136 may determine the speed of the vehicle system 100 from location data provided by the location determining device 120. This location data may represent locations of the vehicle system 100 at different times, and the control system, location determining device 120, and/or detection device 136 may calculate the speed of the vehicle system 100 from this data.

The moving speed of the vehicle system 100 can be used by the detection device 136 to determine if several changes of interest are caused by the speed of the vehicle system 100. For example, the route 102 may include regularly occurring gaps that are not caused by damage to the route 102. A track formed from rails can be divided into similarly sized segments that are divided from one another by gaps to permit the rails to expand during increased heat to prevent the rails from contacting and buckling. If several changes of interest identified by the detection device 136 occur at a rate that corresponds to the speed of the vehicle system 100, then these changes of interest may be identified as being indicative of travel of the wheels 114 over the gaps in the route 102 and not damage to the route 102. For example, if the changes of interest repeatedly occur at rates that increase when the speed of the vehicle system 100 increases and/or rates that decrease when the vehicle system 100 slows down, then the detection device 136 may determine that the changes of interest reflect travel over the gaps and not damage to the route 102.

Another example of reference tracking includes modifying the designated frequencies, designated decibel levels, and/or designated thresholds used to identify the changes of interest using vehicle control events. The detection device 136 may change which frequencies in the acoustic signatures are examined for a step change, frequency change, or tonal change indicative of damage to the route 102 based on the speed and/or acceleration of the vehicle system 100. For example, as the vehicle system 100 speeds up, the detection device 136 may examine larger frequencies in the acoustic signatures for step changes, frequency changes, or tonal changes indicative of damage to the route 102. The increased speeds of the vehicle system 100 may cause the passively excited residual sounds generated by the wheels 114 traveling over damaged sections of the route 102 to generate higher pitched tones or sounds. Conversely, as the vehicle system 100 slows down, the detection device 136 may examine smaller frequencies in the acoustic signatures for step changes, frequency changes, or tonal changes indicative of damage to the route 102. The decreased speeds of the vehicle system 100 may cause the passively excited residual sounds generated by the wheels 114 traveling over damaged sections of the route 102 to generate lower pitched tones or sounds.

Another example of reference tracking includes modifying the designated frequencies, designated decibel levels, and/or designated thresholds used to identify the changes of interest using vehicle control events. The detection device 136 may change which frequencies in the acoustic signatures are examined for a step change, frequency change, or tonal change indicative of damage to the route 102 based on the speed and/or acceleration of the vehicle system 100. For example, as the vehicle system 100 speeds up, the detection device 136 may examine larger frequencies in the acoustic signatures for step changes, frequency changes, or tonal changes indicative of damage to the route 102. The increased speeds of the vehicle system 100 may cause the passively excited residual sounds generated by the wheels 114 traveling over damaged sections of the route 102 to generate higher pitched tones or sounds. Conversely, as the vehicle system 100 slows down, the detection device 136 may examine smaller frequencies in the acoustic signatures for step changes, frequency changes, or tonal changes indicative of damage to the route 102. The decreased speeds of the vehicle system 100 may cause the passively excited residual sounds generated by the wheels 114 traveling over damaged sections of the route 102 to generate lower pitched tones or sounds.

The formulation device 134 may create several different acoustic signatures for several different pickup devices 126 and the detection device 136 may separately examine these acoustic signatures for changes of interest. For example, the formulation device 134 may generate one or more first acoustic signatures for the pickup device 126A and one or more second acoustic signatures for the pickup device 126B using passively excited residual sounds that are sensed at the same time or approximately the same time by the respective pickup devices 126A, 126B. The detection device 136 may examine the first acoustic signatures to identify changes of interest associated with the residual sounds sensed by the pickup device 126A and examine the second acoustic signatures to identify changes of interest associated with the residual sounds sensed by the pickup device 126B. Optionally, the acoustic signatures may be created from multiple pickup devices 126 disposed onboard different vehicles of a vehicle consist. For example, the vehicle system 100 may include multiple vehicles mechanically coupled together, such as in a rail vehicle consist. The pickup devices 126 disposed on different vehicles in the consist may sense residual sounds which may be used to create the acoustic signatures that are examined by the detection device 136.

The detection device 136 can compare the temporal separation between the changes of interest in the acoustic signatures associated with the respective pickup devices 126 with the speeds and/or accelerations of the vehicle system 100 to determine if the changes of interest in the acoustic signatures represent the same potential damage in the route 102. For example, the first pickup device 126A may travel ahead of the second pickup device 126B along a direction of travel of the vehicle system 100. The detection device 136 may determine that the first acoustic signature of the first pickup device 126A includes a change of interest at a first time and the second acoustic signature of the second pickup device 126B includes a change of interest at a second time. The detection device 136 can examine the time difference between when the change of interest in the first acoustic signature occurs and when the change of interest in the second acoustic signature occurs and compare this time difference to the distance between the first and second pickup devices 126A, 126B and the speed and/or acceleration of the vehicle system 100. If this time difference corresponds to this distance and speed and/or acceleration (e.g., the time difference is equal or approximately equal to the distance between the pickup devices 126A, 126B divided by the speed of the vehicle system 100), then the detection device 136 may determine that the changes of interest represent the same potential damage to the route 102. For example, the detection device 136 may use multiple changes of interest detected by several pickup devices 126 in order to confirm detection of a potentially damaged section of the route 102.

Responsive to the detection device 136 identifying one or more changes of interest in the acoustic signatures, an identification device 138 identifies damage to the route 102 and/or confirms an identification of damage to the route 102 by another detection system. The identification device 138 may associate one or more changes of interest with damage to the route 102. For example, detection of a step change, a tonal change, or a frequency change in the acoustic signatures may cause the identification device 138 to determine that the route 102 is damaged, such as by having a break in the route 102, a crack in the route 102, pitting in the route 102, voids inside the route 102, bends in the route 102 (e.g., in a rail of the route 102), or the like. The acoustic signatures and/or changes of interest in the acoustic signatures may be associated with times at which the residual sounds represented by the signatures and/or changes were detected. For example, the signatures and/or changes of interest may be time-stamped. The identification device 138 may compare the times at which the changes of interest occur with the locations of the vehicle system 100 at the same or similar times (as detected by signals received by the location determining device 120). Using this comparison, the identification device 138 can determine where the identified damage is located along the route 102. For example, the damage may be identified as being located at or relatively near the location where the vehicle system 100 was disposed when the change of interest indicative of the damage was sensed by the pickup device(s) 126.

In one aspect, the identification device 138 can identify the type of damage to the route 102 based on the change of interest that is identified by the detection device 136. The identification device 138 may access template acoustic signatures stored in the memory device 140 (or otherwise accessible to the identification device 138). These template acoustic signatures may represent empirically derived acoustic signatures, acoustic signatures derived from mathematical models, or other acoustic signatures that are representative of different types of damage to the route 102. If the detection device 136 determines that a change of interest is present in an acoustic signature formed by the signature formulation device 134, then the identification device 138 may compare all or a part of the acoustic signature (e.g., at least the portion that includes the change of interest) to one or more of the template acoustic signatures. The identification device 138 may determine which of the template acoustic signatures more closely matches the actual acoustic signature (e.g., has peaks, valleys, and/or steps at one or more of the same or similar frequencies as the actual acoustic signature). The type of damage that is associated with the template acoustic signature that more closely matches the actual acoustic signature (or that is the closest match to the actual acoustic signature) may be identified by the identification device 138 as the damage to the route 102.

Figure 6:
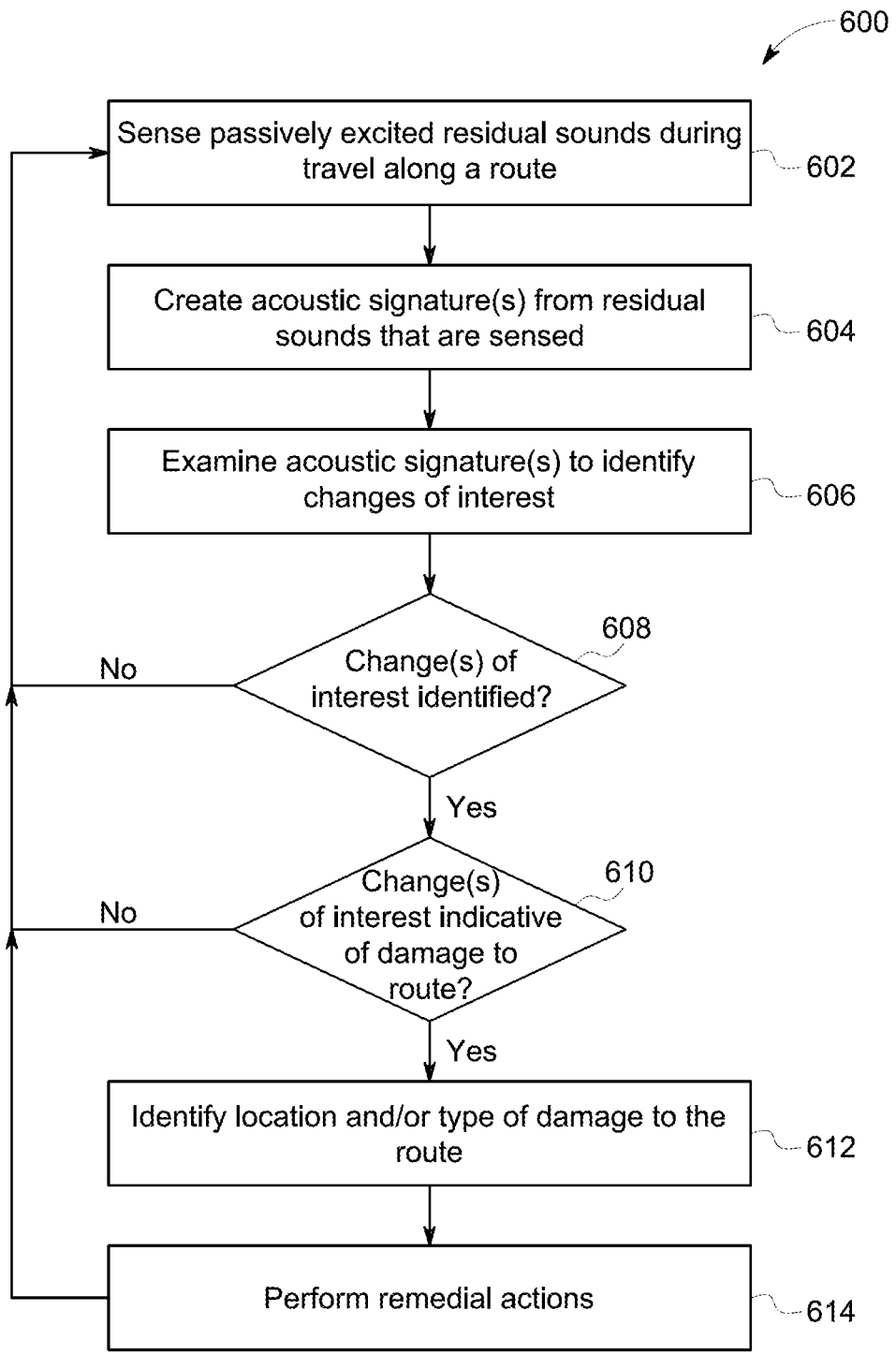
FIG. 6 illustrates a flowchart of a method for examining a route using passively excited residual noises of a vehicle system.

FIG. 6 illustrates a flowchart of a method 600 for examining a route using passively excited residual noises of a vehicle system. The method 600 may be used in conjunction with the route damage detection system 132 to detect and/or identify damaged sections of the route 102. The method 600 may be used to create a software algorithm, package, or system that can be used to direct one or more processors to perform the actions described herein. For example, the operations of the method 600 may represent actions to be performed by one or more processors under direction of the software algorithm, package, or system. At least one technical effect of the methods described herein includes the detection and/or identification of damaged sections of a route using passively excited residual sounds.

At 602, passively excited residual sounds are sensed during travel of the vehicle system 100 along the route 102. As described above, these sounds may be generated by movement of the vehicle system 100 and not generated for the sole purpose of examining the route 102. For example, these sounds may include the sounds of the wheels 114 traveling over the route 102, the propulsion system 116 operating to propel the vehicle system 100, and the like. Alternatively, at least some of these sounds may include background or white noise that is generated to drown out changes in the passively excited residual sounds generated by operation of the vehicle system 100.

At 604, one or more acoustic signatures 200 are generated from the residual sounds that are sensed. The acoustic signatures can represent an average, median, or other measure of the residual sounds over a period of time, or can represent the residual sounds at a point in time. Several acoustic signatures may be generated from multiple different sets of residual sounds that are sensed by different pickup devices 126 located in different locations of the vehicle system 100.

At 606, the acoustic signatures are examined to identify changes of interest. As described above, the entire frequency spectrum of an acoustic signature may be examined or one or more subsets of this spectrum may be examined. The subsets of frequencies that are examined may be based on the vehicle control events (e.g., speeds, accelerations, throttle settings, brake settings, and the like) of the vehicle system 100, the size of the vehicle system 100, the type of damage that is to be identified, and the like. The changes of interest can include step changes, frequency changes, tonal changes, or other changes in the decibels and/or frequencies of the acoustic signatures.

At 608, a determination is made as to whether one or more changes of interest are identified from the acoustic signatures. If one or more changes of interest are identified, then the changes may indicate that the vehicle system 100 has traveled over a damaged portion of the route 102. Consequently, flow of the method 600 may proceed to 610. On the other hand, if no changes of interest are identified, or if the changes occur outside of one or more frequency subsets of the acoustic signatures that are associated with different types of damage to the route 102, then the changes and/or acoustic signatures may not indicate damage to the route 102. As a result, flow of the method 600 can return to 602 so that additional residual sounds can be sensed.

At 610, the changes of interest are examined to determine if the changes indicate damage to the route 102. For example, the frequencies at which the changes of interest occur may be examined to determine if these frequencies match or correspond with the frequencies that are empirically determined to match or correspond to damage to the route 102. As another example, template acoustic signatures that represent one or more types of damage to the route 102 may be compared to the changes of interest to determine if the changes of interest match the template acoustic signatures. A match may indicate that the changes of interest represent the type of damage to the route 102 with which the template acoustic signature(s) are associated.

If the changes of interest are associated with damage to the route 102, then the residual sounds that were sensed can indicate that the route 102 is damaged. As a result, flow of the method 600 can proceed to 612. If the changes of interest are not associated with damage to the route 102, then the residual sounds may not indicate damage to the route 102. Consequently, flow of the method 600 may return to 602 so that additional residual sounds can be sensed.

In one aspect, identification of the damage to the route 102 may be used to confirm identification of the damage to the route 102 by another system. For example, another system onboard the same vehicle system 100, another vehicle system, and/or a wayside device may detect damage to the route 102. Such a system may inject an electrical signal into the route 102 on one side of the damaged location and attempt to sense the signal and/or changes to the signal on another side of the damaged location. If the signal is not detected and/or the changes to the signal are detected, then the absence of the signal and/or changes may indicate that the route 102 is damaged (e.g., broken). The residual sounds can be used to confirm or refute the identification of the damaged section by this other system. For example, if both the electrical- and residual noise-based systems detect the damaged section of the route 102, then the route 102 may be identified as being damaged at that location. If only one or neither of these systems detects the damaged section, then the route 102 may not be identified as being damaged at that location.

At 612, the location and/or type of damage to the route 102 that is represented by the changes of interest in the acoustic signatures are determined. The location may be determined by identifying where the vehicle system 100 was located when the changes of interest were sensed by the pickup devices 126. The type of damage to the route 102 can be determined by identifying the frequencies at which the changes of interest occurred and determining the type of damage that is associated with those frequencies (e.g., as empirically determined and/or determined from a model and stored in the memory device 140). Optionally, the type of damage can be determined by identifying which of several template acoustic signatures match or closely match the changes of interest and identifying the damage to the route 102 that is associated with (e.g., identified by) the template acoustic signatures that match or closely match the changes of interest.

At 614, one or more remedial actions are performed. For example, in response to identifying the location and/or type of damage to the route 102, the vehicle system 100 may prompt an operator and/or automatically slow or stop movement to ensure that the vehicle system 100 and/or route 102 are not damaged. As another example, the operator of the vehicle system 100 may be notified via the input/output device 106 of the location and/or type of route damage. The communication device 124 may communicate (e.g., transmit and/or broadcast) a notification of the location and/or type of damage to the route 102. This notification may be sent to an off-board facility, such as a dispatch center. This facility may schedule further inspection of the route 102 at the identified location, re-route other vehicle systems around the damaged location of the route 102, direct other vehicle systems to slow down at or near the damaged location of the route 102, and the like. The notification may be received by other vehicle systems to warn the vehicle systems of the damaged location of the route 102 so that these vehicle systems can slow down, stop, or otherwise avoid travel over the damaged section of the route 102.

In an embodiment, a method (e.g., for acoustically examining a route) includes sensing passively excited residual sounds of a vehicle system during travel over a route using one or more acoustic pickup devices, examining the passively excited residual sounds to identify one or more changes of interest in the passively excited residual sounds using one or more processors of a deviation detection device operably connected with the one or more acoustic pickup devices, and automatically identifying a section of the route as being damaged responsive to the one or more changes of interest in the passively excited residual sounds that are identified using one or more processors of an identification device. The one or more acoustic pickup devices may automatically generate electric signals (e.g., voltages, alternating currents, or the like) that represent the passively excited residual sounds. The one or more acoustic pickup devices can be operably connected with the one or more processors of the deviation detection device by one or more wired and/or wireless connections or networks. The deviation detection device and the identification device may share one or more of the same processors.

In one aspect, the passively excited residual sounds are sounds generated by operation of a propulsion system of the vehicle system to propel the vehicle system and sounds generated by movement of wheels of the vehicle system along the route.

In one aspect, the passively excited residual sounds are sensed with one or more acoustic pickup devices coupled to the vehicle system that are spaced apart from the route and acoustically coupled with the route by air.

In one aspect, the method also includes identifying one or more subsets of designated frequencies at which the passively excited residual sounds are to be examined in order to identify the one or more changes of interest using one or more vehicle control events.

In one aspect, the one or more vehicle control events include at least one of a speed, an acceleration, a throttle setting, or a brake setting of the vehicle system.

In one aspect, the passively excited residual sounds are sensed from a first location within a designated target measurement area extending from where a wheel of the vehicle system engages the route and from a second location disposed outside of the designated target measurement area.

In one aspect, the one or more changes of interest include at least one of a step change, a frequency change, or a tonal change in one or more frequencies of the passively excited residual sounds.

In one aspect, the method also includes comparing the one or more changes of interest to one or more template acoustic signatures representative of sounds generated when a wheel travels over a corresponding one or more designated types of damage to the route and identifying a type of damage to the route that is indicated by the one or more changes of interest from the one or more designated types of damage based on which of the one or more template acoustic signatures more closely matches the one or more changes of interest relative to others of the one or more template acoustic signatures.

In one aspect, the method also includes confirming identification of the section of the route as being damaged by another system that examines the route without using the passively excited residual sounds.

In an embodiment, a system (e.g., for acoustically examining a route) includes a deviation detection device and an identification device. The deviation detection device is configured to receive passively excited residual sounds of a vehicle system sensed by one or more acoustic pickup devices during travel over a route. The deviation detection device also is configured to examine the passively excited residual sounds to identify one or more changes of interest in the passively excited residual sounds. The identification device is configured to identify a section of the route as being damaged responsive to the one or more changes of interest in the passively excited residual sounds that are identified by the deviation detection device.

In one aspect, the passively excited residual sounds are sounds generated by operation of a propulsion system of the vehicle system to propel the vehicle system and sounds generated by movement of wheels of the vehicle system along the route.

In one aspect, the passively excited residual sounds are sensed with the one or more acoustic pickup devices that are coupled to the vehicle system and that are spaced apart from the route and acoustically coupled with the route by air.

In one aspect, the deviation detection device is configured to identify one or more subsets of designated frequencies at which the passively excited residual sounds are to be examined in order to identify the one or more changes of interest using one or more vehicle control events.

In one aspect, the passively excited residual sounds are sensed from a first location within a designated target measurement area extending from where a wheel of the vehicle system engages the route and from a second location disposed outside of the designated target measurement area.

In one aspect, the one or more changes of interest include at least one of a step change, a frequency change, or a tonal change in one or more frequencies of the passively excited residual sounds.

In one aspect, the identification device is configured to compare the one or more changes of interest to one or more template acoustic signatures representative of sounds generated when a wheel travels over a corresponding one or more designated types of damage to the route and to identify a type of damage to the route that is indicated by the one or more changes of interest from the one or more designated types of damage based on which of the one or more template acoustic signatures more closely matches the one or more changes of interest relative to others of the one or more template acoustic signatures.

In an embodiment, a method (e.g., for examining a route) includes generating an acoustical signature of audible passively excited residual sounds generated by movement of a vehicle system along a route, examining one or more subsets of frequencies of the audible passively excited residual sounds in the acoustical signature to identify one or more changes of interest, and identifying a section of the route as being damaged using the one or more changes of interest.

In one aspect, the audible passively excited residual sounds are generated by a propulsion system of the vehicle system that propels the vehicle system and movement of one or more wheels of the vehicle system along the route.

In one aspect, the method also includes selecting the one or more subsets of frequencies of the audible passively excited residual sounds to examine based on at least one of more of a speed, acceleration, throttle setting, or brake setting of the vehicle system.

In one aspect, the method also includes comparing the one or more changes of interest to different template acoustical signatures representative of sounds generated during travel of the vehicle system over corresponding different types of damage to the route and identifying a type of damage to the section of the route based on one of the template acoustical signatures that matches the one or more changes of interest more closely than one or more other template acoustical signatures.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hard-wired to perform the methods or portions of the methods described herein, and/or when the processors (e.g., of the devices described herein) operate according to one or more software programs that are written by one or more persons of ordinary skill in the art to perform the operations described in connection with the methods.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described systems and methods without departing from the spirit and scope of the inventive subject matter herein involved, it is intended that all of the subject matter of the above description or shown in the accompanying drawings shall be interpreted merely as examples illustrating the inventive concept herein and shall not be construed as limiting the inventive subject matter.

The invention claimed is:

1. A method comprising:
sensing passively excited residual sounds of a vehicle system during travel over a route using one or more acoustic pickup devices, wherein a previous acoustic signature represents the passively excited residual sounds sensed during a period of time and a subsequent acoustic signature represents the passively excited residual sounds sensed subsequent to the period of time;
examining the passively excited residual sounds to identify one or more changes of interest in the passively excited residual sounds using one or more processors of a deviation detection device operably connected with the one or more acoustic pickup devices, wherein the one or more chances of interest that are identified include one or more of:
  a step change representative of a decrease or elimination of one or more frequencies in the subsequent acoustic signature, wherein the one or more frequencies have greater magnitudes in the previous acoustic signature than in the subsequent acoustic signature, or
  a frequency change representative of a shift of one or more peaks from the one or more frequencies in the previous acoustic signature to one or more different frequencies in the subsequent acoustic signature; and automatically identifying a section of the route as being damaged responsive to the one or more changes of interest in the passively excited residual sounds that are identified using one or more processors of an identification device.

2. The method of claim 1, wherein the passively excited residual sounds are sounds generated by operation of a propulsion system of the vehicle system to propel the vehicle system and sounds generated by movement of wheels of the vehicle system along the route.

3. The method of claim 1, wherein the passively excited residual sounds are sensed with one or more acoustic pickup devices coupled to the vehicle system that are spaced apart from the route and acoustically coupled with the route by air.

4. The method of claim 1, further comprising identifying one or more subsets of designated frequencies at which the passively excited residual sounds are to be examined in order to identify the one or more changes of interest using one or more vehicle control events.

5. The method of claim 4, wherein the one or more vehicle control events include at least one of a speed, an acceleration, a throttle setting, or a brake setting of the vehicle system.

6. The method of claim 1, wherein the passively excited residual sounds are sensed from a first location within a designated target measurement area extending from where a wheel of the vehicle system engages the route and from a second location disposed outside of the designated target measurement area.

7. The method of claim 1, wherein the one or more changes of interest include a tonal change in the one or more frequencies of the passively excited residual sounds.

8. The method of claim 1, further comprising:
comparing the one or more changes of interest to one or more template acoustic signatures representative of sounds generated when a wheel travels over a corresponding one or more designated types of damage to the route; and
identifying a type of damage to the route that is indicated by the one or more changes of interest from the one or more designated types of damage based on which of the one or more template acoustic signatures more closely matches the one or more changes of interest relative to others of the one or more template acoustic signatures.

9. The method of claim 1, further comprising confirming identification of the section of the route as being damaged by another system that examines the route without using the passively excited residual sounds.

10. The method of claim 1, further comprising:
determining when control events of the vehicle system occur, the control events including one or more of a throttle setting, a brake setting, an acceleration, a deceleration, a vehicle speed, an on state of a motor, or an off state of the motor;
temporally correlating at least one of the control events with one or more of the passively excited residual sounds; and
eliminating at least one of the changes of interest from being used to identify the section of the route as being damaged based on a correlation between the one or more of the passively excited residual sounds and the at least one of the control events.

11. A system comprising:
a deviation detection device configured to receive passively excited residual sounds of a vehicle system sensed by one or more acoustic pickup devices during travel over a route, the deviation detection device configured to examine the passively excited residual sounds to identify one or more changes of interest in the passively excited residual sounds, wherein a previous acoustic signature represents the passively excited residual sounds sensed during a period or time and a subsequent acoustic signature represents the passively excited residual sounds sensed subset subsequent to the period of time, and wherein the one or more changes of interest that are identified include one or more of:
a step change representative of a decrease or elimination of one or more frequencies in the subsequent acoustic signature, wherein the one or more frequencies have greater magnitudes in the previous acoustic signature than in the subsequent acoustic signature, or
a frequency change representative of a shift of one or more peaks from the one or more frequencies in the previous acoustic signature to one or more different frequencies in the subsequent acoustic signature; and
an identification device configured to identify a section of the route as being damaged responsive to the one or more changes of interest in the passively excited residual sounds that are identified by the deviation detection device.

12. The system of claim 11, wherein the passively excited residual sounds are sounds generated by operation of a propulsion system of the vehicle system to propel the vehicle system and sounds generated by movement of wheels of the vehicle system along the route.

13. The system of claim 11, wherein the passively excited residual sounds are sensed with the one or more acoustic pickup devices that are coupled to the vehicle system and that are spaced apart from the route and acoustically coupled with the route by air.

14. The system of claim 11, wherein the deviation detection device is configured to identify one or more subsets of designated frequencies at which the passively excited residual sounds are to be examined in order to identify the one or more changes of interest using one or more vehicle control events.

15. The system of claim 11, wherein the passively excited residual sounds are sensed from a first location within a designated target measurement area extending from where a wheel of the vehicle system engages the route and from a second location disposed outside of the designated target measurement area.

16. The system of claim 11, wherein the one or more changes of interest include a tonal change in the one or more frequencies of the passively excited residual sounds.

17. The system of claim 11, wherein the identification device is configured to compare the one or more changes of interest to one or more template acoustic signatures representative of sounds generated when a wheel travels over a corresponding one or more designated types of damage to the route and to identify a type of damage to the route that is indicated by the one or more changes of interest from the one or more designated types of damage based on which of the one or more template acoustic signatures more closely matches the one or more changes of interest relative to others of the one or more template acoustic signatures.

18. A method comprising:
generating an acoustical signature of audible passively excited residual sounds generated by movement of a vehicle system along a route;
selecting one or more subsets of frequencies of the audible passively excited residual sounds to examine based on one or more of a speed, acceleration, throttle setting, or brake setting of the vehicle system examining the one or more subsets of frequencies of the audible passively excited residual sounds in the acoustical signature that are selected to identify one or more changes of interest; and identifying a section of the route as being damaged using the one or more changes of interest.

19. The method of claim 18, wherein the audible passively excited residual sounds are generated by a propulsion system of the vehicle system that propels the vehicle system and movement of one or more wheels of the vehicle system along the route.

20. The method of claim 18, further comprising:

comparing the one or more changes of interest to different template acoustical signatures representative of sounds generated during travel of the vehicle system over corresponding different types of damage to the route; and identifying a type of damage to the section of the route based on one of the template acoustical signatures that matches the one or more changes of interest more closely than one or more other template acoustical signatures.

* * * * *